US009112926B2

(12) United States Patent
Kerger et al.

(10) Patent No.: US 9,112,926 B2
(45) Date of Patent: Aug. 18, 2015

(54) RECOMMENDING MOBILE CONTENT BY MATCHING SIMILAR USERS

(75) Inventors: Kameron N. Kerger, San Diego, CA (US); Daniel J. Guest, San Diego, CA (US); Scott D. Beith, Carlsbad, CA (US); Jee Young P. Wipperfurth, San Francisco, CA (US)

(73) Assignee: QUALCOMM, Incorporated, San Diego, CA (US)

( * ) Notice: Subject to any disclaimer, the term of this patent is extended or adjusted under 35 U.S.C. 154(b) by 63 days.

(21) Appl. No.: 13/079,529

(22) Filed: Apr. 4, 2011

(65) Prior Publication Data

US 2012/0254246 A1 Oct. 4, 2012

(51) Int. Cl.
| | | |
|---|---|---|
| *G06F 7/00* | (2006.01) |
| *H04L 29/08* | (2006.01) |
| *H04W 4/20* | (2009.01) |
| *H04W 4/18* | (2009.01) |
| *G06F 19/00* | (2011.01) |

(52) U.S. Cl.
CPC ............... *H04L 67/306* (2013.01); *H04W 4/18* (2013.01); *H04W 4/206* (2013.01); *G06F 19/705* (2013.01)

(58) Field of Classification Search
CPC .................... G06F 17/30575; G06F 17/30174; G06F 17/30581; G06F 17/30578; G06F 11/2097
USPC .......................................................... 707/622
See application file for complete search history.

(56) References Cited

U.S. PATENT DOCUMENTS

| 7,870,186 B2 | 1/2011 | Park |
| 2006/0233063 A1 | 10/2006 | Inoue et al. |
| 2007/0073837 A1* | 3/2007 | Johnson-McCormick et al. ............... 709/217 |
| 2008/0052371 A1 | 2/2008 | Partovi et al. |
| 2009/0177651 A1* | 7/2009 | Takamatsu et al. ............... 707/5 |
| 2010/0191682 A1* | 7/2010 | Takamatsu ...................... 706/12 |

FOREIGN PATENT DOCUMENTS

| EP | 1708200 A1 | 10/2006 |
| JP | 2001175718 A | 6/2001 |
| JP | 2001229285 A | 8/2001 |
| JP | 2002334257 A | 11/2002 |
| JP | 2006277880 A | 10/2006 |
| JP | 2008176406 A | 7/2008 |
| JP | 2010157207 A | 7/2010 |

(Continued)

OTHER PUBLICATIONS

International Search Report and Written Opinion—PCT/US2012/031617—ISA/EPO—Jul. 5, 2012.

(Continued)

*Primary Examiner* — Truong Vo
(74) *Attorney, Agent, or Firm* — Shirin Tefagh

(57) ABSTRACT

A content recommendation apparatus and method gives users a peer-to-peer, highly personal way to discover new content by being introduced to one or more similar users. A similar user is a user that has a correlation to another user based on their preferences and behaviors (e.g., downloaded content, frequency of use, content currently have on device, browsing behaviors, content organizational habits, etc.). A catalog of content, or a designated portion thereof, can be used at least in part for finding matches and for identifying content to suggest to another. Data about user behavior can serve to connect the user to similar individuals for the purpose of discovering new content.

51 Claims, 13 Drawing Sheets

(56) References Cited

FOREIGN PATENT DOCUMENTS

| | | |
|---|---|---|
| JP | 2011511982 A | 4/2011 |
| KR | 100562427 B1 | 3/2006 |
| KR | 20060106683 A | 10/2006 |
| KR | 20090072575 A | 7/2009 |
| WO | 2008129606 A1 | 10/2008 |
| WO | 2009097153 A1 | 8/2009 |

OTHER PUBLICATIONS

Schafer J., et al., "Collaborative Filtering Recommender Systems", Apr. 24, 2007, The Adaptive Web; [Lecture Notes in Computer Science; LNCS], Springer Berlin Heidelberg, Berlin, Heidelberg, p. 291-324, XP019057885, ISBN: 978-3-540-72078-2 [ retrieved on May 16, 2007] sections 9.2 and 9.4.1.

* cited by examiner

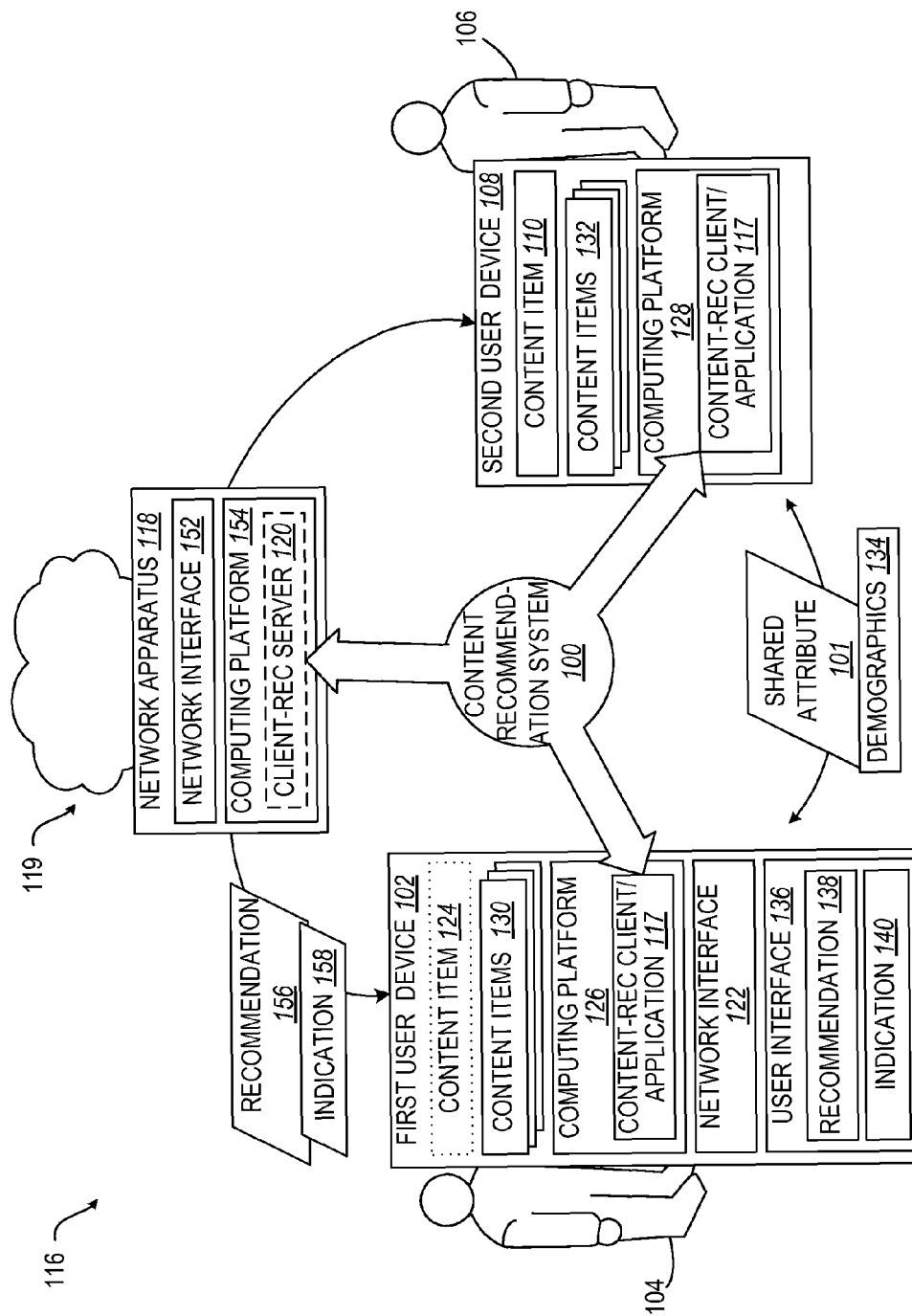

RECOMMENDING MOBILE CONTENT BY MATCHING SIMILAR USERS

The present disclosure relates to a mobile operating environment, and more particularly, to providing improved apparatus and methods of distributing content to user devices, and more particularly to recommending content appropriate to a particular user of a user device.

Mobile operators or mobile device carriers play a major part in the telecommunication industry today. Initially, such mobile operators concentrated their efforts on generating revenue by increasing their subscriber base. However, it will be appreciated that in several countries the scope for increasing the subscriber base has now become very limited, as the market has reached close to saturation point. As a result, the mobile operators have been branching into providing value added services to subscribers, in order to increase their revenue.

One means of generating increased revenue is through the sales of premium services to users, such as ringtones, wallpaper, games, etc. These services may be provided by the mobile operators themselves, or by business entities who may operate in collaboration with the mobile operators to provide such services. The services may be available for download to a user's mobile device upon payment of a fee.

Many benefits such as maximizing the potential earnings for sales may accrue upon recommending and promoting to users content or services that are the most likely to be of interest to the users. The user can have a better experience using the user's mobile device in light of these individually recommended content and services. What users need is a way to discover new content that is easy to use, hopefully fun, and yet still relevant. One way to solve this problem is through an application recommendation system. This can work, but it is still based on an aggregated "average" of user behavior and preferences. Such recommendations can be wholly unsuited to users with particular skill sets and interests that differ from the norm.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In one aspect, the present disclosure provides a method for recommending content by identifying as similar a second user of a second user device to a first user of a first user device. Content used by the second user device that has not been used by the first user device is identified. The content is recommended to the first user device.

In another aspect, the present disclosure provides at least one processor for recommending content. A first module identifies as similar a second user of a second user device to a first user of a first user device. A second module identifies content used by the second user device that has not been used by the first user device. A third module recommends the content to the first user device.

In an additional aspect, the present disclosure provides a computer program product for recommending content comprising a non-transitory computer-readable storage medium. At least one instruction causes a computer to identify as similar a second user of a second user device to a first user of a first user device. At least one instruction causes the computer to identify content used by the second user device that has not been used by the first user device. At least one instruction causes the computer to recommend the content to the first user device.

In a further aspect, the present disclosure provides an apparatus for recommending content. The apparatus comprises means for identifying as similar a second user of a second user device to a first user of a first user device. The apparatus comprises means for identifying content used by the second user device that has not been used by the first user device. The apparatus comprises means for recommending the content to the first user device.

In yet another aspect, the present disclosure provides an apparatus for recommending content. An interface selectively obtains data about a population of users of user devices. A content recommender identifies as similar a second user of a second user device to a first user of a first user device based on the data. The content recommender further identifies content used by the second user device that has not been used by the first user device based on the data. The content recommender further recommends the content to the first user device.

In yet an additional aspect, the present disclosure provides a method for recommending content by receiving, at a network, data associated with a first user of a first user device and a second user of a second user device of a population of user devices. The second user of the second user device is identified as similar to the first user of the first user device. Content used by the second user device that has not been used by the first user device is identified. The content is recommended to the first user device.

In yet a further aspect, the present disclosure provides at least one processor for recommending content. A first module receives, at a network, data associated with a first user of a first user device and a second user of a second user device of a population of user devices. A second module identifies as similar the second user of the second user device to the first user of the first user device. A third module identifies content used by the second user device that has not been used by the first user device. A fourth module recommends the content to the first user device.

In one aspect, the present disclosure provides a computer program product for recommending content comprising a non-transitory computer-readable storage medium. At least one instruction causes a computer to receive, at a network, data associated with a first user of a first user device and a second user of a second user device of a population of user devices. At least one instruction causes the computer to identify as similar the second user of the second user device to the first user of the first user device. At least one instruction causes the computer to identify content used by the second user device that has not been used by the first user device. At least one instruction causes the computer to recommend the content to the first user device.

In another aspect, the present disclosure provides an apparatus for recommending content. The apparatus comprises means for receiving, at a network, data associated with a first user of a first user device and a second user of a second user device of a population of user devices. The apparatus comprises means for identifying as similar the second user of the second user device to the first user of the first user device. The apparatus comprises means for identifying content used by the second user device that has not been used by the first user device. The apparatus comprises means for recommending the content to the first user device.

In a further aspect, the present disclosure provides an apparatus for recommending content. A network interface receives, at a network, data associated with a first user of a first user device and a second user of a second user device of a population of user devices. A content recommender identifies as similar the second user of the second user device to the first user of the first user device. The content recommender further identifies content used by the second user device that has not been used by the first user device. The network interface further recommends the content to the first user device.

To the accomplishment of the foregoing and related ends, the one or more aspects comprise the features hereinafter described in detail and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 1 illustrates a schematic diagram of an application recommendation system, according to one aspect.

DETAILED DESCRIPTION

Figure 2A:
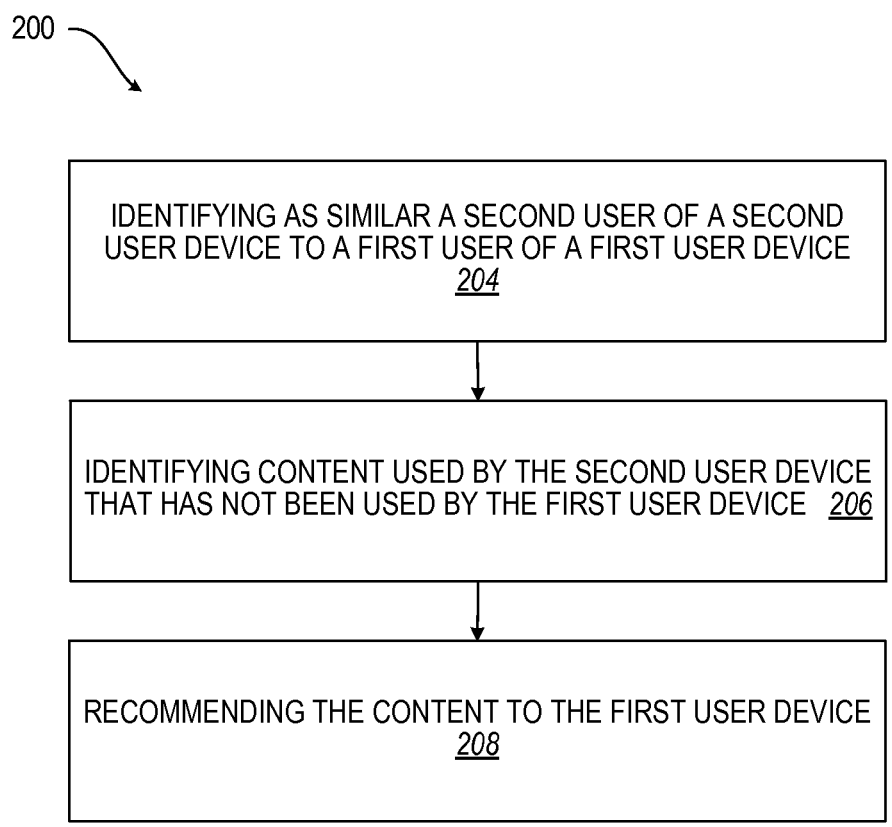
FIG. 2A illustrates a flow diagram for a method of recommending applications, according to one aspect.

In accordance with one or more aspects and corresponding disclosure thereof, various aspects are described in connection with recommending particular content for user equipment to download. Content can comprise various media digital formats, either singularly or in multimedia compositions, of video, audio, image, textual, and haptic including Braille, etc. Content can also comprise application software (e.g., utilities, games, office productivity, social networking, etc.). The described apparatus and methods match user preferences and behaviors to uniquely generated user profiles, which are used to enhance discovery of mobile content. Thereby strangers can be turned into a content recommendation service, and perhaps turning strangers with similar interests in content into personal acquaintances.

In particular, the recommendations are not based upon a bland aggregation of all user behavior or an impersonal calculation made by a network provider. Instead, a user, or a group of users to varying degrees, of the described apparatus and methods is determined to be a substantial match with one or more users based on the described matching. With a recommendation made based upon usage by a similar user or users, a user friendly and fun way is provided to discover new and relevant content in a crowded content ecosystem marketplace.

In an exemplary aspect, the present disclosure gives users a peer-to-peer and highly personal way to discover new content by being introduced to similar user(s). A similar user is a user that has a correlation to another user or users based on their preferences and behaviors. These preferences and behaviors can be, but are not limited to, content items users have downloaded, frequency of use of the content items, content items a user currently has on the device, browsing behaviors, content organizational habits, and more. A similar user application or service may introduce users to these similar user(s) and may allow them to "peek" into all or part of the content catalog that the other user has on the user's device. Such discovery of content on a similar user device may allow the user to discover "hidden gems" that the similar user has, but the user had not yet discovered.

In alternative or additional aspects, the service may then mark the similar users as more like the user or less like the user via a sliding scale. The scaled similar user rankings may then be used to enhance and discover even more content in the future.

The described apparatus and methods provide a fun and enticing way to discover new content, such as shopping for new applications, audiovisual media content, textual news, blogging content, etc. In other words, the described apparatus and methods utilize data about a user (e.g., user behavior, etc.) to connect like individuals for the purpose of discovering new content.

In a further aspect, a network service that facilitates the described apparatus and methods may also gain key insights into user behavior as well as learn more about how users may or may not be alike. Increased revenue can be achieved through alternate discovery streams. The service can build a trusted relationship for other types of recommendations or promotions for services or content.

Moreover, a user of the described apparatus and methods benefits by readily finding suitable content in an intuitive fashion, similar to word of mouth recommendations or promotions by providing a virtual or real world introduction to similarly situated individuals. A better means of discovery narrows down the vast choices in a content/application catalog. Further, the recommendations can appeal to a person's inherent voyeuristic needs or qualities.

Various aspects are now described with reference to the drawings. In the following description, for purposes of explanation, numerous specific details are set forth in order to provide a thorough understanding of one or more aspects. It may be evident, however, that the various aspects may be practiced without these specific details. In other instances, well-known structures and devices are shown in block diagram form in order to facilitate describing these aspects.

With initial reference to FIG. 1, an exemplary content recommendation system 100 is depicted, according to one aspect. The content recommendation system 100 operates to recommend content to a first user device 102 based upon determining shared attribute(s) 101 with another user or another user device, where the recommended content corresponds to a content item 110 defined on the other user device. For example, system 100 may identify shared attribute(s) 101 between a first user 104 of the first user device 102 and a second user 106 of a second user device 108 who uses content item 110 not used by the first user 104 or defined the first user device 102.

The second user 106 can be deemed to have used the content item 110 based upon having overtly selected the content item 110 for download, installation, or activation. Alternatively or in addition, the second user 106 can be deemed to have used the content item 110 based upon a reported count of times the content item 110 has been executed, run, played, viewed, or presented. Alternatively or in addition, the second user 106 can be deemed to have used the content item 110 based upon a reported count of user interactions with the content item 110, such as a count of key clicks or menu selections. Alternatively or in addition, the second user 106 can be deemed to have used the content item 110 based upon a reported amount of elapsed time in which the content item 110 has been executed, run, played, viewed, or presented.

System 100 thereby recommends content item 110 to the first user 104 or the first user device 102 in response to determining a match between the first user 104 and the second user 106 or the first user device 102 and the second user device 108 (e.g., based on shared attribute(s) 101 and determining that content item 110 is not associated with the first user 104 or the first user device 102 but may be of interest based on shared attribute(s) 101). Accordingly, the content recommendation system 100 is part of a communication system 116 used to identify and match the shared attribute(s) 101 of the first user 104 and the second user 106. It should be noted that the communication system 116 can further be used for other types of packet data communication (e.g., text messaging, voice communication, Internet access, etc.).

In one aspect, the content recommendation system 100 can operate as a stand-alone apparatus, such as a content recommendation client/application 117 on the first user device 102 and the second user device 108 that form an ad hoc communication session in order to determine the shared attribute(s) 101. Alternatively or in addition, a network apparatus 118 can provide access to a network 119 for the first user device 102 and the second user device 108, and act as an intermediary for communication services, in general. In a further aspect, the network apparatus 118 can include a content recommendation server 120 that ascertains the shared attribute(s) 101 for the first user device 102 and the second user device 108.

It should be noted that for clarity, the exemplary content recommendation system 100 is described with certain functions performed by the first user device 102 and the second user device 108 and others centralized at the network apparatus 118. However, implementations consistent with the present disclosure can distribute functions described herein wholly or substantially in the first user device 102 and the second user device 108, wholly or substantially in a single or distributed network apparatus 118, or dynamically shifted between the first user device 102 and the second user device 108 and the network apparatus 118. For example, for the first user device 102 and the second user device 108 that are mobile, certain functions can be dependent upon what network access is being used or whether the first user device 102 and the second user device 108 are physically in proximity to one another.

In one aspect, a network interface 122 of the first user device 102 ascertains at least one of the shared attribute(s) 101 of the first user 104, the shared attribute(s) 101 of the second user 106, a content item (or lack thereof as depicted at 124) of a first computing platform 126 of the first user device 102, and the content item 110 of a second computing platform 128 of the second user device 108.

Thus, the network interface 122 serves as an interface for selectively obtaining data about a population of users of user devices. Alternatively or in addition, the network interface 122 can serve as the interface for communicating with a network that processes the data and is remote to the first user device 102 and the second user device 108. Alternatively or in addition, the network interface 122 serves for provisioning the first user device 102 with content from the network. Alternatively or in addition, the network interface 122 serves as an interface for provisioning the first user device 102 with content from the second user device 108 by performing peer-to-peer networking.

In an exemplary aspect, the shared attribute(s) 101 pertains to usage of content items 130 of the first user device 102 and content items 132 of the second user device 108. Shared attribute(s) 101 can be an extent to which the content items 130 and content items 132 match or otherwise indicate user similarities (e.g., similar genres of content items 110, etc.).

Alternatively, the shared attribute(s) 101 can be an aspect not directly related to the content items 130 and content items 132. For example, the first user 104 can begin using a first user device 102 that has no content items 110 or a ubiquitous default grouping of content items 110 that do not indicate shared attribute(s) 101. However, in one example, user demographics 134, which can include express user inputs or implicit behavior, can serve at least in part as the shared attribute(s) 101.

The first computing platform 126 having matched, or having been informed of a match, between the first and second users 104 and 106, identifies the content item 110 of the second user device 108 that could be of interest to the first user 104. In particular, a user interface 136 presents a recommendation 138 for the content item 110. The user interface 136 can thus be for presenting a promotion for content. In one aspect, an indication 140 is also presented to identify the second user 106 that served as a basis for a presented recommendation 138 about the identified (selected) content item 110.

In one aspect, the network apparatus 118 of the network 119 has a network interface 152 and computing platform 154 for performing or facilitating the matching of first and second users 104 and 106, identifying the content item 110, and transmitting a recommendation 156 to the first user device 102. In addition, the network apparatus 118 can transmit an indication 158 of an identity, alias or other characteristics about the second user 106 to the first user device 102 to bolster the perceived reliability of the recommendation 156.

In FIG. 2A, a methodology 200 is depicted for recommending content, according to one aspect. A second user of a second user device is identified as similar to a first user of a first user device (block 204). Content used by the second user device that has not been used by the first user device is identified (block 206). The content is recommended to the first user device (block 208).

Figure 2B:
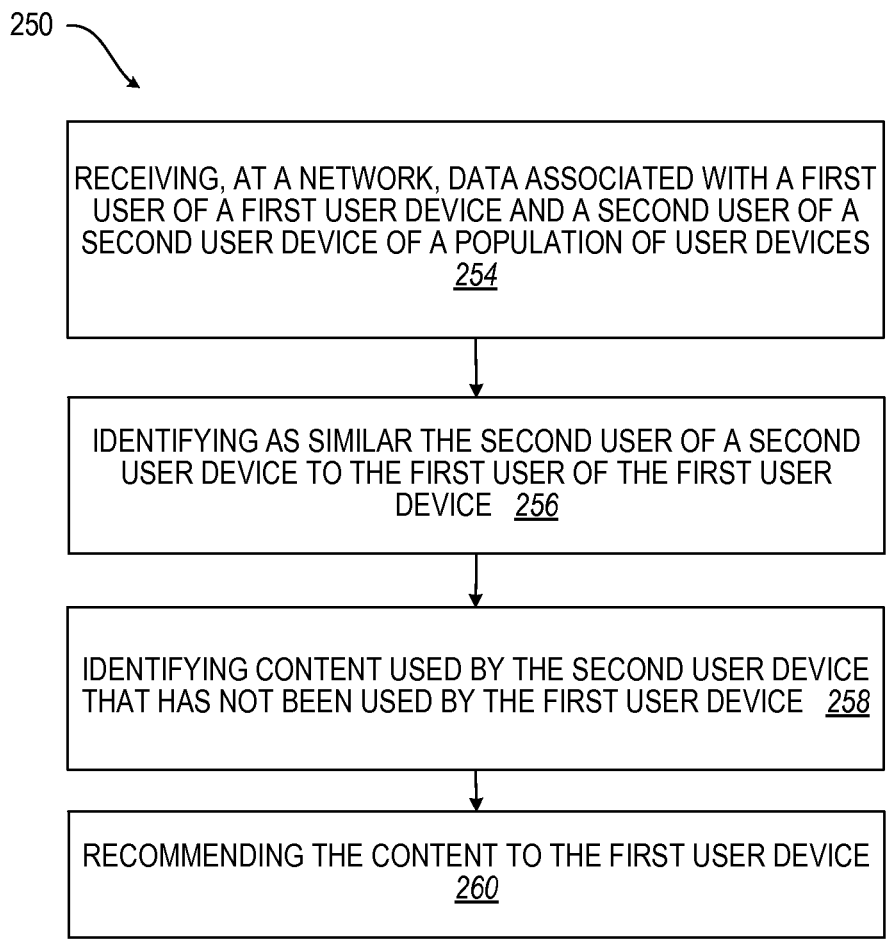
FIG. 2B illustrates a flow diagram for a method of transmitting a recommendation for applications, according to one aspect.

In FIG. 2B, a methodology 250 is depicted for recommending content, according to yet another aspect. Data is received at a network associated with a first user of a first user device and a second user of a second user device of a population of user devices (block 254). The second user of the second user device is identified as similar to the first user of the first user device (block 256). Content used by the second user device is identified that has not been used by the first user device (block 258). The content is recommended to the first user device (block 260).

It is contemplated according to certain aspects of the present disclosure that the recommendation can be a promotion. As another example, the recommendation can indicate to the first user that the second user was determined to be similar to the first user.

As an additional example, the similarity between users can be found by matching a demographic category. Alternatively or in addition, the similarity can be found by matching content on the first user device to content on the second user device. In particular, the matching for similarity purposes can focus on content actually used or used frequently on the respective user devices. Similarity can be by determining that a count of matching content exceeds a threshold. Alternatively, a ratio of matching content can be compared to a threshold.

The content recommended or used for finding similarity can be a software application. Alternatively or in addition, the content recommended can be media content. Alternatively or in addition, the content recommended or used for finding similarity can be an advertisement for goods or services.

In some instances, recommending content can be dependent upon determining proximity of the first and second users, such as being able to perform peer-to-peer networking between the first and second user devices. Facilitating interaction between user devices or for informing users of the user devices can be dependent upon one or both allowing the interaction via a user interface input.

Content recommendation can entail processing data performed largely or entirely on the user device, remote to the user device, or a distributed processing between the user device and remote entities on the network. For example, communicating between the network and the first user device can be performed at least in part via a Wireless Wide Area Network (WWAN), Wireless Local Area Network (WLAN) or Personal Area Network (PAN) communication link. The network can also provide a content download system.

Figure 3:
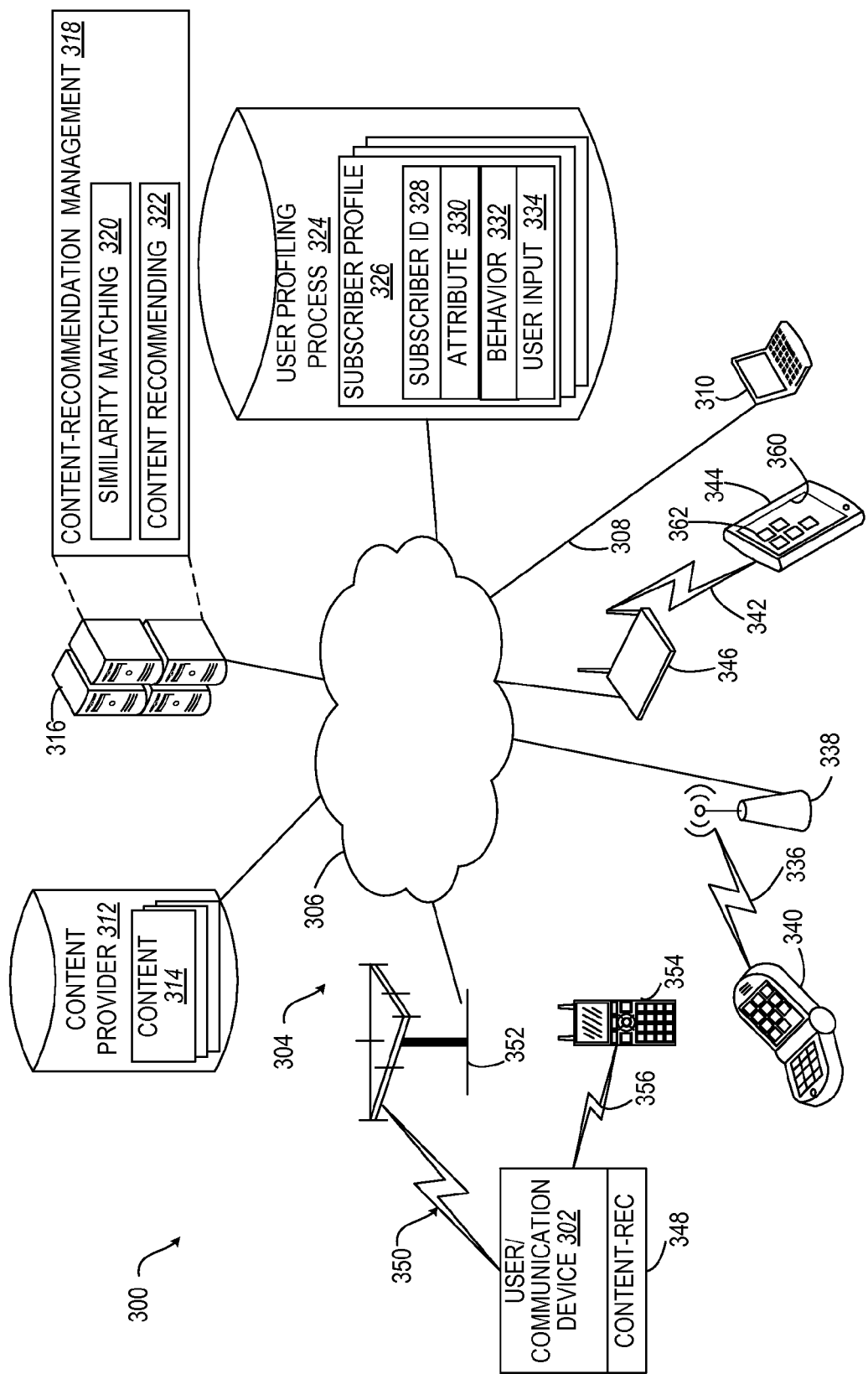
FIG. 3 illustrates a schematic diagram of a content recommendation system operating over a mixed technology communication system, according to one aspect.

In FIG. 3, according to one aspect, a content recommendation system 300 is depicted for recommending content for executing on a communication device or user device 302 based upon finding a similar user or users. In particular, a communication system 304 upon which the content recommendation system 300 operates is illustrated as potentially using various technologies and processing arrangements to track users, determine similarities, compare content on user devices, and to recommend content.

For clarity, a cloud network 306 is depicted as serving as communication hub. For example, a public or private packet data network (e.g., a first or second generation Internet, Public Switch Telephone Network (PSTN), etc.) can interconnect portions of the content recommendation system 300. Alternatively or in addition, certain entities within the content recommendation system 300 can be interconnected or exchange information with the cloud network 306 via wired connection(s) 308, such as communication device or user device 310, which can be fixed or mobile.

Network entities that participate with, give support to, or are constituents of the content recommendation system 300 can include a content provider 312, depicted as a data repository containing content 314. For another example, a network entity can comprise a content recommendation server 316 that can execute a content recommendation management component 318 having a similarity matching component 320 and a content recommending component 322. For an additional example, a network entity can comprise a user profiling process 324 that generates and maintains information pertaining to user or subscriber profiles 326. For instance, subscriber profiles 326 can comprise subscriber identification 328, identified attributes (e.g., demographic categories) 330, behavior data (e.g., content purchased, used, etc.) 332, and/or user inputs (e.g., ratings, social network/blog entries, biometric indications of interest, etc.) 334.

Alternatively in addition to wired connection(s) 308, a wireless link (e.g., WLAN, PAN, etc.) 336 to an access point 338 can be used by communication device or user device 340. Alternatively or in addition, a restricted cell connection 342 for communication device 344 can be provided by a femtocell 346. The communication device or user device 302 can incorporate a client content recommendation component 348 that interacts with the network entities (e.g., content provider 312, content recommendation server 316, and user profiling process 324). Alternatively or in addition to the already mentioned types of communication links, communication device or user device 302 can utilize a WWAN or cellular link 350 to a base node 352. Alternatively or in addition, a communication device or user device 354 can participate in the content recommendation system 300 via a peer-to-peer (P2P) connection 356.

User devices 302, 310, 340, 344, 354 are illustrated as various types of computing platforms with respective user interfaces 360 that enable consumption or use of content 362. It should be appreciated with the benefit of the present disclosure that these illustrative types are not all inclusive and that a great variety of devices and distributed systems can perform aspects of the present disclosure.

Figure 4:
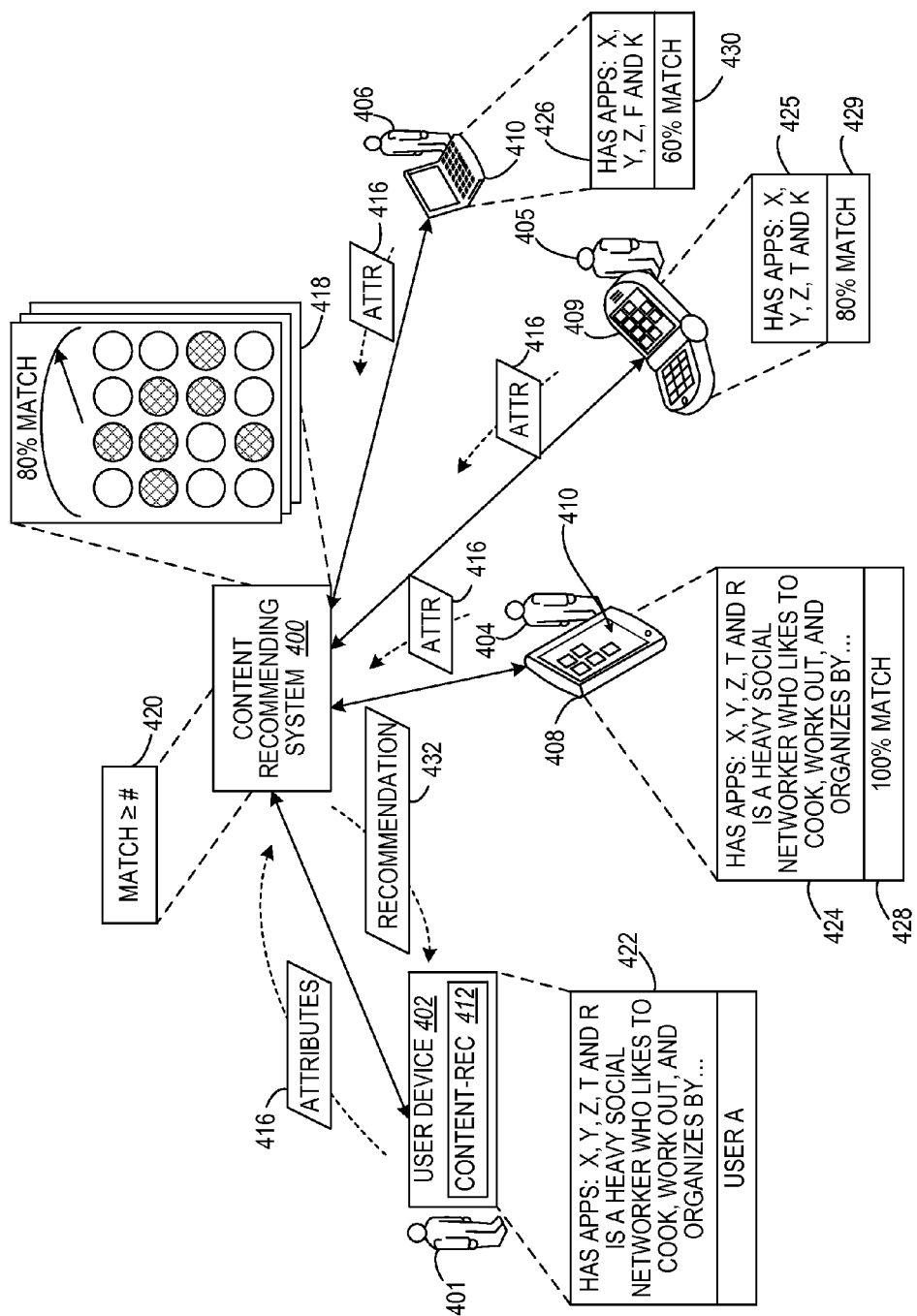
FIG. 4 illustrates a functional block diagram for a scenario employing the content recommendation system of FIG. 3, according to one aspect.

In FIG. 4, an illustrative scenario, a content recommending system 400 is depicted, which, on behalf of a first user 401 of a first communication device or first user device 402, finds similar users, depicted as second user 404, third user 405, and fourth user 406, of respective communication devices, second user device 408, third user device 409, and fourth user device 410, to the first user 401 of the first user device 402. The content recommendation system 400 can be substantially or wholly performed by a client content recommendation component 412 on the first user device 402, which can be capable of operating autonomously for certain periods of time. Alternatively or in addition, the content recommendation system 400 can be substantially or wholly performed remotely.

Attributes 416 respectively about the first user 401 of the first user device 402, the second user 404 of the second user device 408, the third user 405 of the third user device 409, and the fourth user 406 of the fourth user device 410 are collected by the content recommendation system 400. These attributes 416 can pertain to one or more of content stored on or used on the first user device 402, the second user device 408, the third user device 409, and the fourth user device 410. In addition, or alternatively, the attributes 416 can pertain to behavior of the first user 401, the second user 404, the third user 405, and the fourth user 406. The attributes 416 can pertain to inferred, cross referenced or submitted demographic information about the first user 401, the second user 404, the third user 405, and the fourth user 406, etc. In the illustrative scenario, the content is primarily used for determining similarity. For instance, the content recommendation system 400 can perform matching as depicted at 418 wherein similarities between content items (e.g., applications, media content, etc.) are determined, such as by a ratio of shared content. Alternatively or in addition, a match based on a count of commonly owned or used content is used as depicted at 420.

In use, the first user 401 can be characterized as depicted at 422. In like fashion, the second user 404, the third user 405, and the fourth user 406 can be characterized respectively as depicted at 424, 425, and 426. Each of the second user 404, the third user 405, and the fourth user 406 is quantitatively matched against the first user 401 as depicted respectively at 428, 429, and 430. Depending upon the set threshold, a tradeoff can be made as to the closeness of the match and the number of matching second users. For example, two of the three second users meet or exceed an 80% match. In another aspect, predetermined number (e.g., one) of user can be found that exceeds a threshold or the highest value(s) found among the population of users. Based upon the matching a recommendation 432 can be made to the first user device 402.

Figure 5:
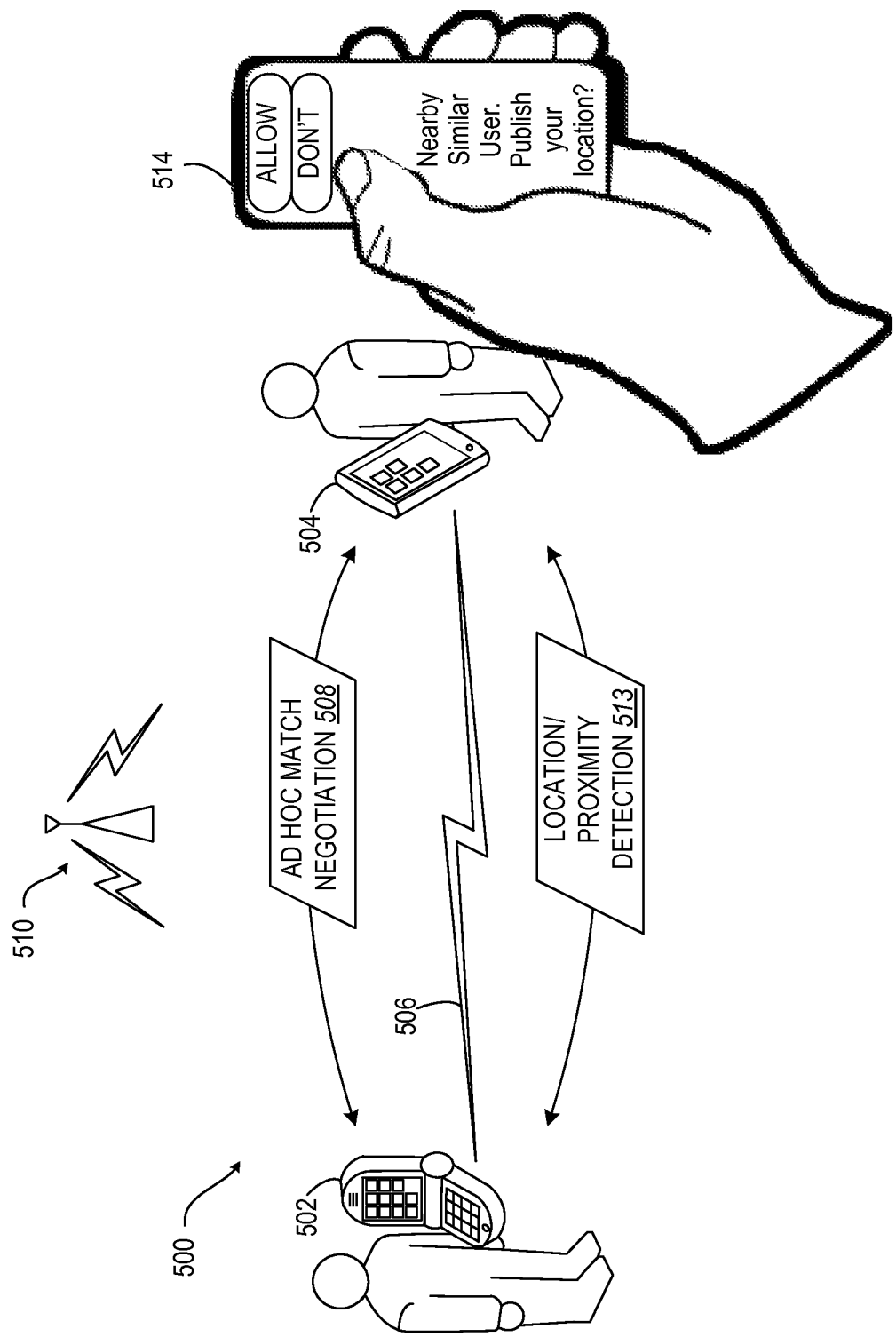
FIG. 5 illustrates a depiction of two user devices performing proximity based recommendation of applications, according to one aspect.

In FIG. 5, in a specific aspect, an ad hoc network 500 can be formed between two users carrying respectively a first wireless mobile device 502 and a second wireless mobile device 504 for providing a geo-location use case. Each of the first wireless mobile device 502 and the second wireless mobile device 504 can be provisioned with ad hoc network capability such as WiFi Peer-To-Peer (P2P) as depicted at 506 with ad hoc network negotiation as depicted by 508. Alternatively, each of the first wireless mobile device 502 and the second wireless mobile device 504 can be provisioned with a P2P capability through an intermediary node 510 (e.g., WWAN macrocell or femtocell node) that indicates proximity of the users to each other.

In an exemplary and non-limiting aspect, each of the first wireless mobile device 502 and the second wireless mobile device 504 is provisioned with a proximate Internet capability system. Both of the first wireless mobile device 502 and the second wireless mobile device 504 use a similar user(s) application at a public place. Using a low power automatic push communication system, the first wireless mobile device 502 can determine there is a possible similar user nearby using a location proximity detection capability 513 and can provide a human perceptible alert (e.g., tactile vibration, signal to a BlueTooth device, visual indication, audible indication, etc.). Each user can be given an opportunity to agree to meeting the similar user. In one aspect, a user can select in advance to allow personal alerts or alerts to other users. In another aspect, each user can select to allow the meeting when a nearby similar user is identified as depicted at 514. An incentive for meeting face to face can be knowledge that the other user shares some similarity (e.g., applications used) and that the other has some application that could be introduced to the other.

Figure 6:
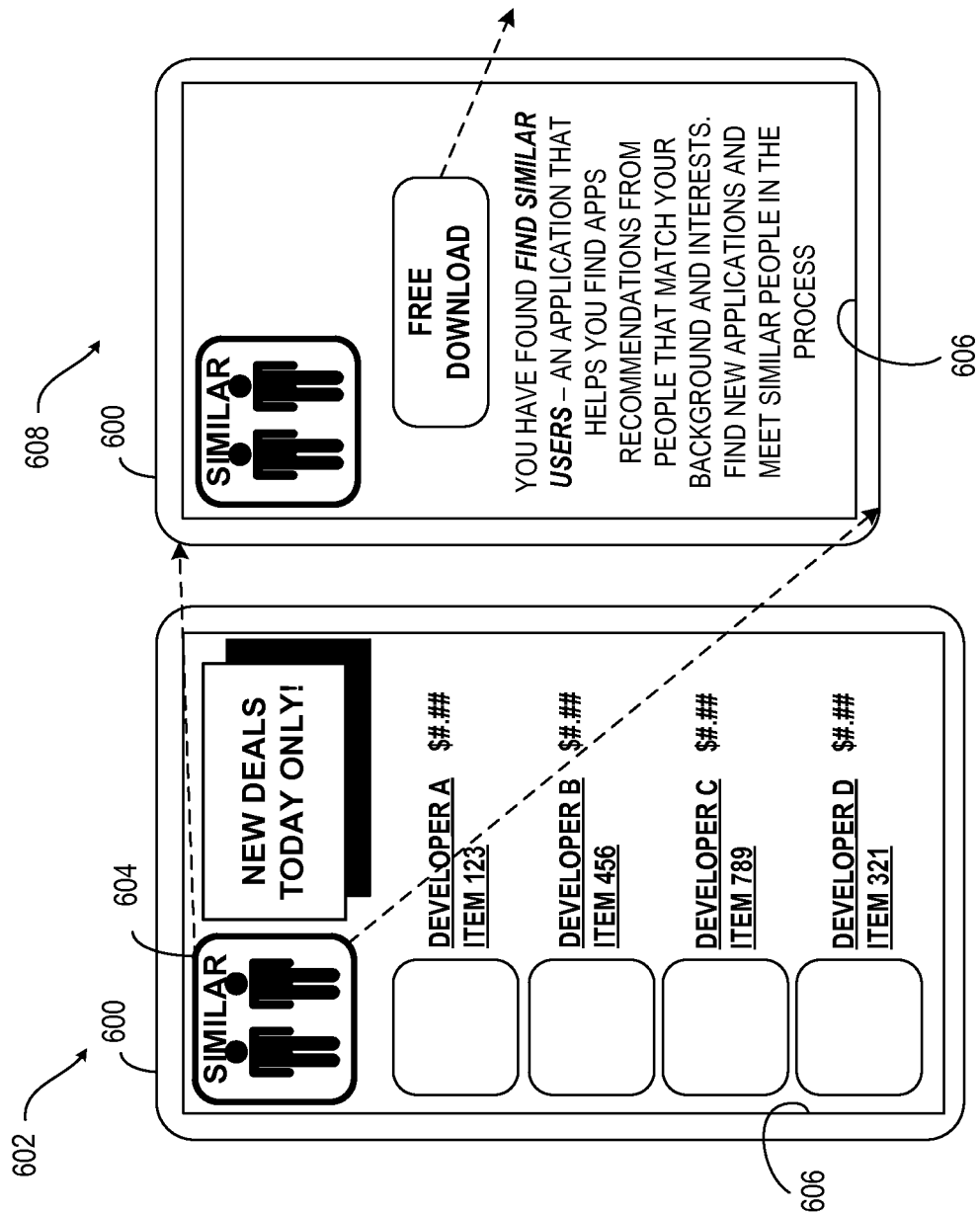
FIG. 6 illustrates a depiction of a user interface for recommending content, according to one aspect.
Figure 7:
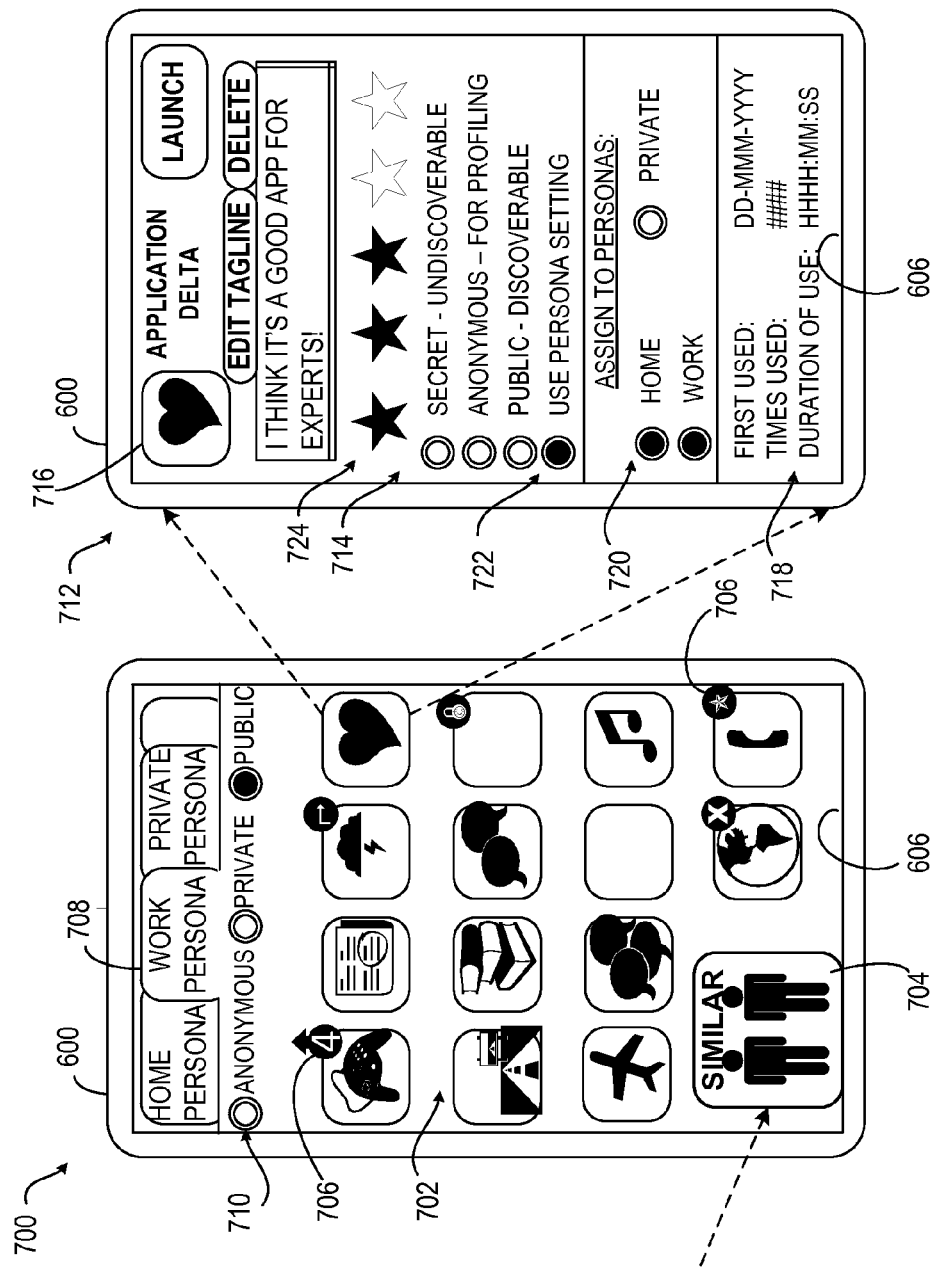
FIG. 7 illustrates a depiction of a user interface for recommending content, according to one aspect.
Figure 8:
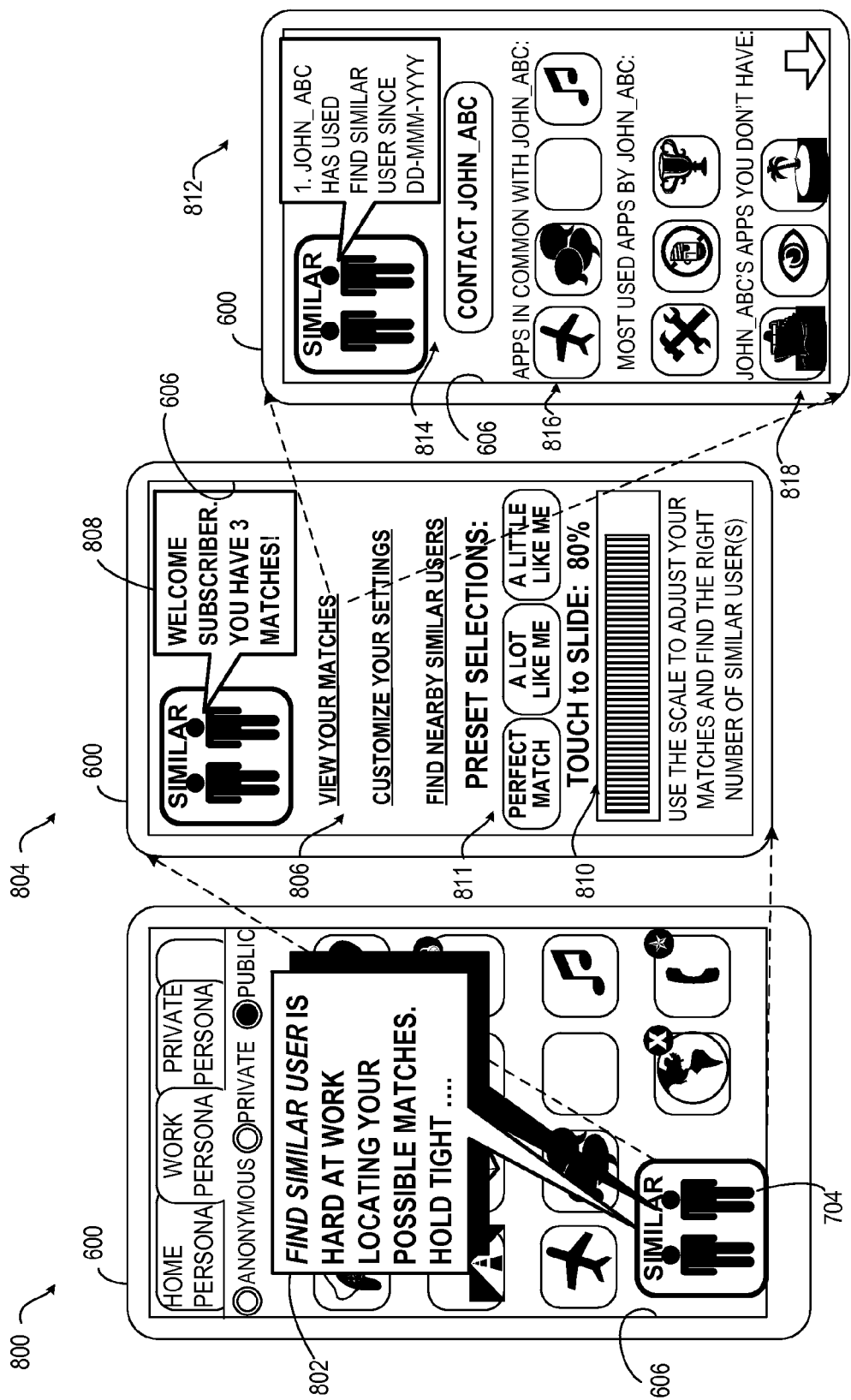
FIG. 8 illustrates a depiction of a user interface for recommending content, according to one aspect.

In FIGS. 6-8, an illustrative scenario is provided for performing similarity matching and content recommendations based upon applications loaded on a user/communication device, according to one aspect. It should be appreciated that this scenario is illustrative and that more generally, similarity matching can be performed based upon a range of attributes associated with the user or content on the user device. In addition, content recommendations can be for one or more types of content (e.g., media content, applications, etc.).

In FIG. 6, an illustrative user device 600 at an initial state 602 presents a similar users icon 604 on a user interface 606. When selected, a second state 608 is presented wherein the user interface 606 provides an opportunity to download and install the similar user(s) application.

Continuing in FIG. 7, in a third state 700 the user interface 606 displays downloaded applications icons 702, which now includes a similar user(s) application 704. Annotations 706 on the downloaded applications icons 702 can denote a tailored status for interacting with the similar user(s) application 704. The downloaded applications icons 702 can be displayed in subsets or personas 708 that are tailored for particular users, particular user interests or activities, or for particular privacy considerations 710.

In a fourth state 712, the user interface 606 provides a similar users screen 714 for interacting with a particular application 716. For instance, metrics 718 for usage can be tracked as a shared attribute for matching or validating a level of expertise for recommending. Controls 720 can specify where the user can find this application (i.e., persona, subset). Privacy controls 722 can specify whether the application is remotely detectable, detectable for profiling the user, publicly discoverable for recommending, or defaults to the persona settings. Controls can also enable express rating 724 of the application.

In FIG. 8, a fifth state 800 is depicted for a scenario in which the similar user(s) application 704 has been activated or otherwise prompted to display a status message 802 indicating a current search being performed for a similar user.

In a sixth state 804, the user interface 606 provides a top-level results screen 806 identifying the number of matches as depicted at 808 for a user selectable or network set sensitivity level, depicted as both a touch scale 810 or pre-set button selections (e.g., Perfect Match, A lot Like Me, Little Bit Like Me, etc.) 811. Options for accessing these matches can include a control for viewing matches, customizing settings, or finding nearby twins.

In a seventh state 812, upon selecting to view matches the user interface 606 depicts a recommendation screen 814 that gives criteria 816 for finding a match and specific application recommendations 818.

Figure 9:
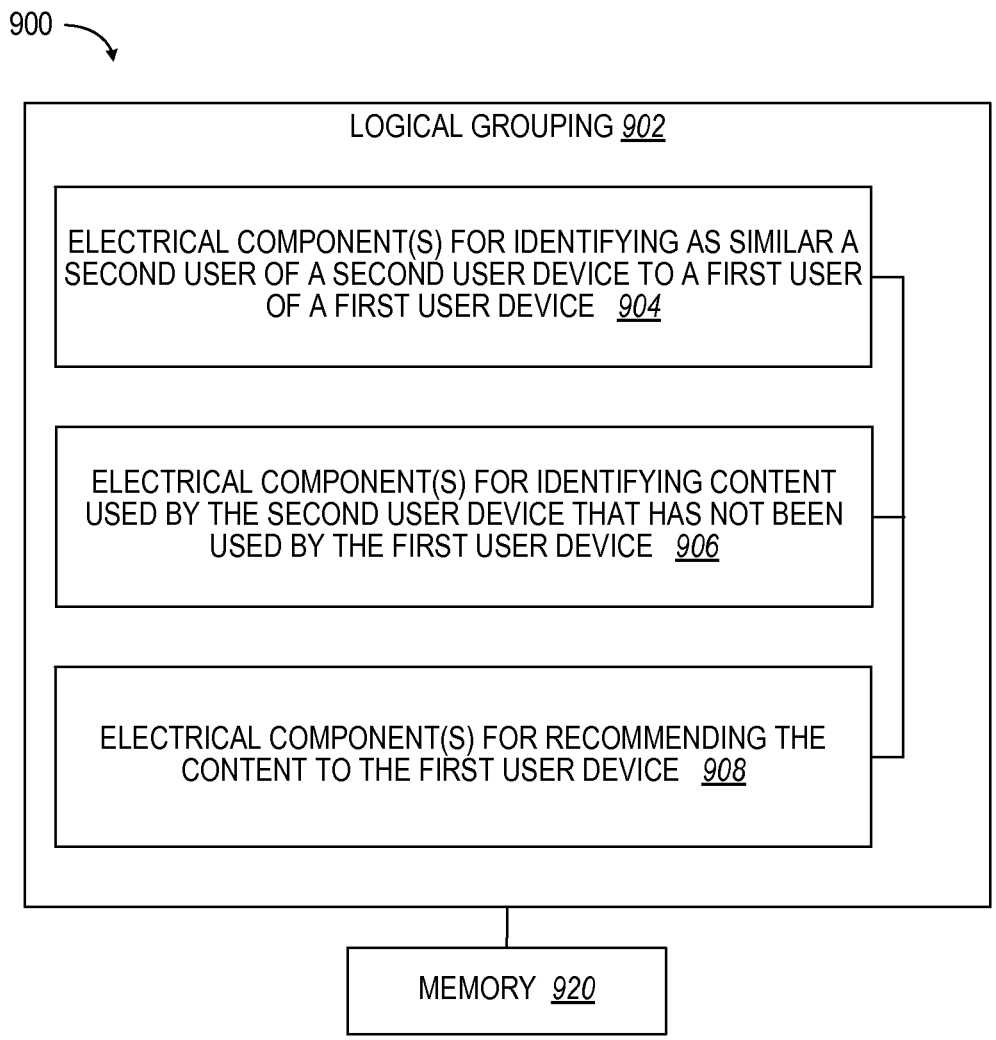
FIG. 9 illustrates a block diagram of a logical grouping of electrical components that resides at least in part in a network entity for recommending content, according to one aspect.

With reference to FIG. 9, illustrated is a system 900 for recommending content. For example, system 900 can reside at least partially within user equipment (UE). It is to be appreciated that system 900 is represented as including functional blocks, which can be functional blocks that represent functions implemented by a computing platform, processor, software, or combination thereof (e.g., firmware). System 900 includes a logical grouping 902 of electrical components that can act in conjunction. For instance, logical grouping 902 can include an electrical component for identifying as similar a second user of a second user device to a first user of a first user device 904. Moreover, logical grouping 902 can include an electrical component for identifying content used by the second user device that has not been used by the first user device 906. Further, logical grouping 902 can include an electrical component for recommending the content to the first user device 908. Additionally, system 900 can include a memory 920 that retains instructions for executing functions associated with the electrical components as depicted at 904, 906, and 908. While shown as being external to memory 920, it is to be understood that one or more of the electrical components depicted at 904, 906, and 908 can exist within memory 920.

Figure 10:
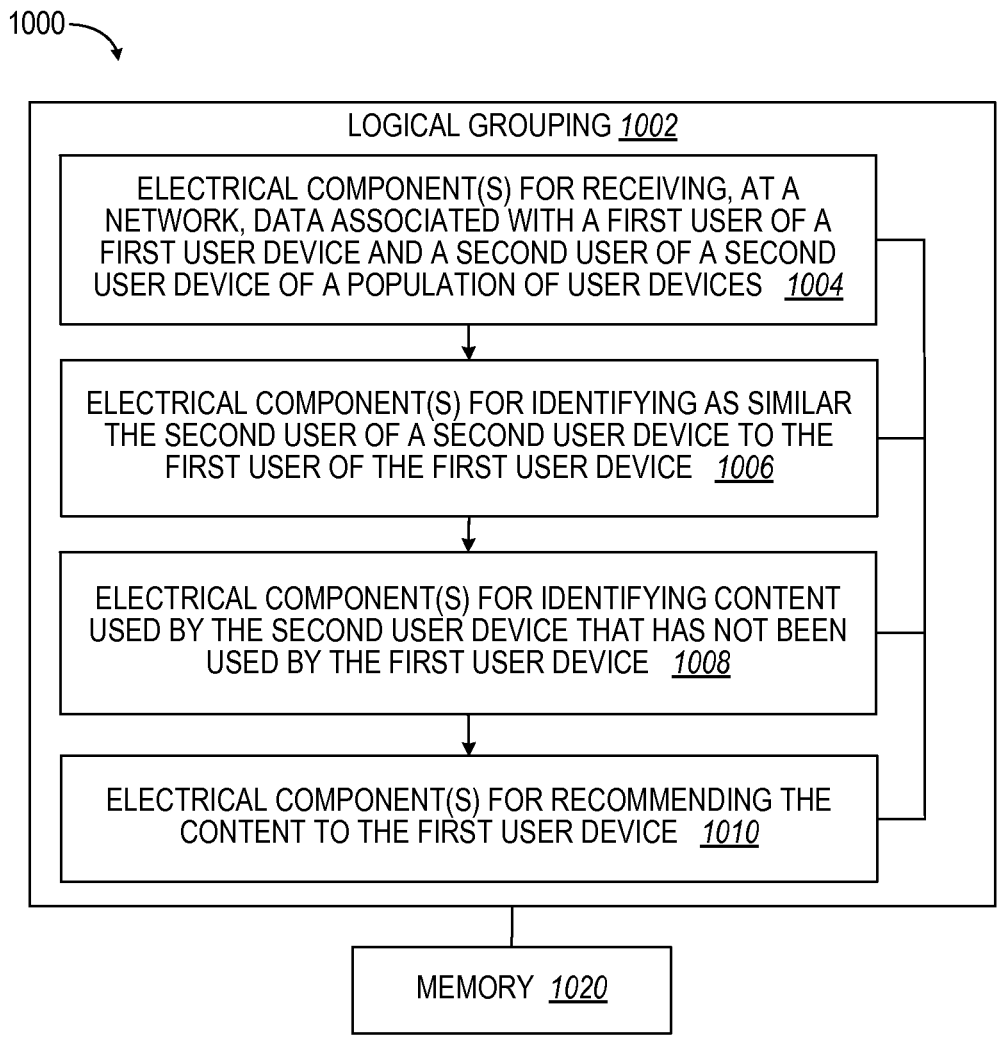
FIG. 10 illustrates a block diagram of a logical grouping of electrical components that resides at least in part in a user device for recommending content, according to one aspect.

With reference to FIG. 10, illustrated is a system 1000 for recommending content, according to one example. For example, system 1000 can reside at least partially within one or more network entities. The system 1000 can comprise a base node that is capable of Over-The-Air (OTA) communication. Aspects disclosed herein for finding similar users and recommending content can be performed at least in part by the base node. Alternatively, such processing can be performed by a network server, such as remotely accessed on a packet data or core network. It is to be appreciated that system 1000 is represented as including functional blocks, which can be functional blocks that represent functions implemented by a computing platform, processor, software, or combination thereof (e.g., firmware). System 1000 includes a logical grouping 1002 of electrical components that can act in conjunction. For instance, logical grouping 1002 can include an electrical component for receiving, at a network, data associated with a first user of a first user device and a second user of a second user device of a population of user devices 1004. Moreover, logical grouping 1002 can include an electrical component for identifying as similar the second user of a second user device to the first user of the first user device 1006. Further, logical grouping 1002 can include an electrical component for identifying content used by the second user device that has not been used by the first user device 1008. For instance, logical grouping 1002 can include an electrical component for recommending the content to the first user device 1010. Additionally, system 1000 can include a memory 1020 that retains instructions for executing functions associated with electrical components 1004, 1006, 1008, and 1010. While shown as being external to memory 1020, it is to be understood that one or more of the electrical components 1004, 1006, 1008, and 1010 can exist within memory 1020.

Figure 11:
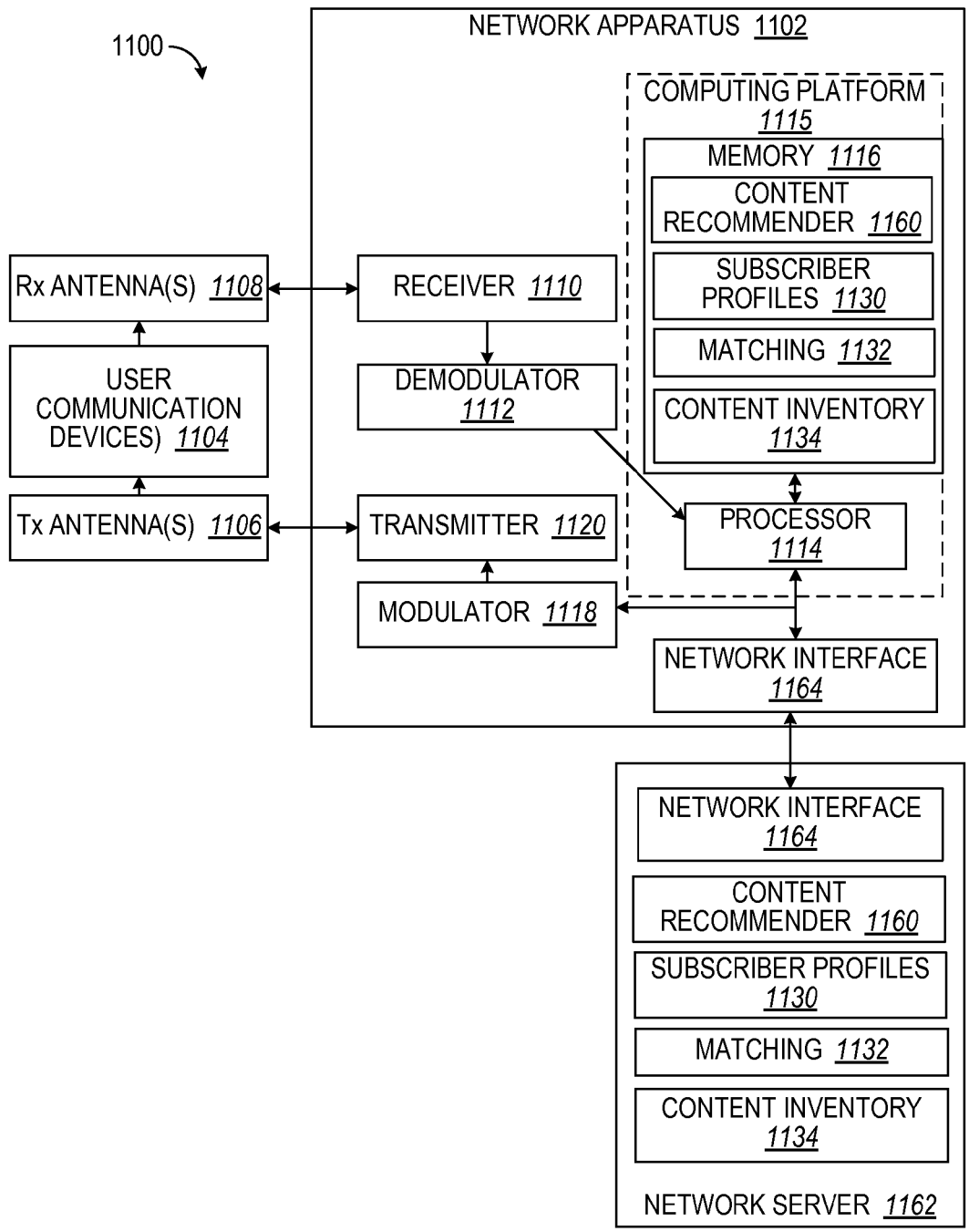
FIG. 11 illustrates a schematic diagram of an exemplary hardware environment of a network entity for recommending content, according to one aspect.

FIG. 11 is a block diagram of a system 1100 that can be utilized to implement various aspects of the functionality described herein. In one example, system 1100 includes a network apparatus (e.g., base node or station) 1102. As illustrated, network apparatus 1102 can receive signal(s) from one or more user communication devices 1104 and transmit to the one or more user communication devices 1104 via one or more antennas 1106. Additionally, network apparatus 1102 can comprise a receiver 1110 that receives information from antenna(s) 1108. In one example, receiver 1110 can be operatively associated with a demodulator 1112 that demodulates received information. Demodulated symbols can then be analyzed by a processor 1114. Processor 1114 of a computing platform 1115 can be coupled to memory 1116, which can store data and/or program codes related to network apparatus 1102. Additionally, network apparatus 1102 can employ processor 1114 to perform methodologies described herein such as a content recommender component 1160. Network apparatus 1102 can also include a modulator 1118 that can multiplex a signal for transmission by a transmitter 1120 through antenna(s) 1106. Subscriber profiles 1130, matching information 1132 and content inventory tracking 1134 can reside in memory for finding recommended applications.

In an exemplary aspect, the content recommender component 1160 is executed on a network server 1162 via network interfaces 1164, remotely to the network apparatus 1102.

Figure 12:
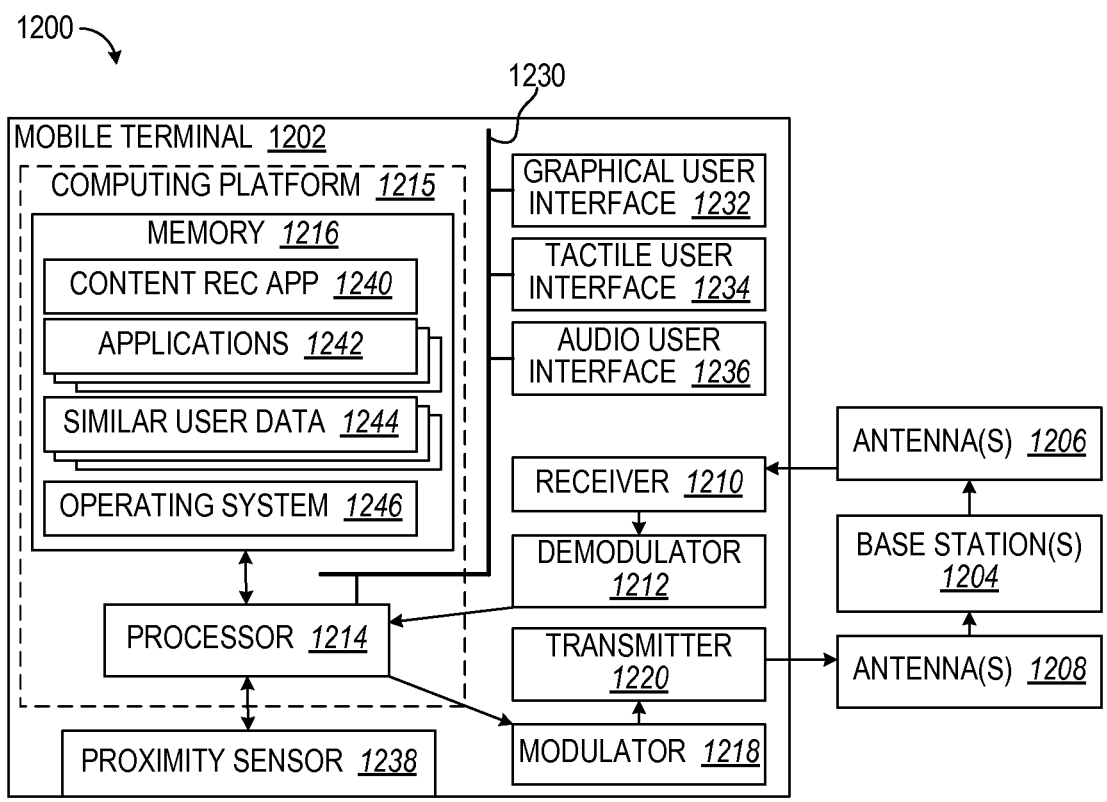
FIG. 12 illustrates a schematic diagram of an exemplary hardware environment of a user device for recommending content, according to one aspect.

FIG. 12 is a block diagram of another system 1200 that can be utilized to implement various aspects of the functionality described herein. In one example, system 1200 includes a user device, communication device, or mobile terminal 1202. As illustrated, mobile terminal 1202 can receive signal(s) from base station(s) 1204 via receive antenna(s) 1206 and transmit to the base station(s) 1204 via transmit antenna(s) 1208. Additionally, mobile terminal 1202 can comprise a receiver 1210 that receives information from receive antenna (s) 1206. In one example, the receiver 1210 can be operatively associated with a demodulator 1212 that demodulates received information. Demodulated symbols can then be analyzed by a processor 1214. Processor 1214 of a computing platform 1215 can be coupled to memory 1216, which can store information related to code clusters, access terminal assignments, lookup tables related thereto, unique scrambling sequences, and/or other suitable types of information. In one example, mobile terminal 1202 can also include a modulator 1218 that can multiplex a signal for transmission by a transmitter 1220 through transmit antenna(s) 1208.

Databus 1230 can interface the processor 1214 to a graphical user interface 1232, a tactile user interface 1234, and an audio user interface 1236. A proximity sensor 1238 can assist in locating nearby similar users. For example, the proximity sensor 1238 can utilize a PAN or WLAN link. Alternatively, the mobile terminal 1202 can utilize information from the base station(s) 1204 to determine that a similar user is in the vicinity based upon Global Positioning System (GPS) information or what cell or sector is providing service. In memory 1216, a similar user component or content recommendation application 1240 can interact with downloaded applications 1242 as well as similar user data 1244 used to customize settings and user attributes. The applications 1240, 1242 can operate upon an operating system 1246.

Those of skill would further appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component", "module", "system", and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In addition, the term application as used herein refers to computer software program in general and can further encompass data, configuration settings, etc., used by the computer software program. Examples include utilities such as e-mail, Short Message Service (SMS) text utility, chat interface, web browsers, calculators, viewers, media players, games, etc. In an exemplary aspect, application can refer to software that is suitable for use on a mobile device, especially to being downloaded via a Wireless Local Access Network (WLAN) or Wireless Wide Area Network (WWAN).

As a further example, applications as used herein can also refer to applets, which can be small programs or applications, usually written in JAVA or ActiveX, that run on a Web browser or other platform independent virtual machine.

As a further example, applications as used herein can also refer to widgets, which can be a code set installed or executed in a webpage without compilation. Examples of widget information which can be downloaded through the Internet include information of weather, traffic, stock, real-time search ranking, photo slide shows, videos, music playlists, post-it notes, horoscopes, and virtual pets, etc. Widgets can be added to social networking profiles, blogs, or Web sites. Examples of types of widgets include (1) a widget engine (such as dashboard applications), (2) GUI widgets (which are a component of a graphical user interface in which the user interacts), (3) Web widgets (which refer to a third party item that can be embedded in a Web page), and (4) mobile widgets (a third party item that can be embedded in a mobile phone). As yet another example, applications as used herein can also refer to triglets.

For clarity, examples herein denote applications that are locally stored on user equipment, mobile devices, handset, access terminals, etc. However, implementations can encompass applications that are remotely stored. Similarly, for clarity distributing of the applications to the mobile devices can be described as being wirelessly downloaded from a WWAN or WLAN or P2P. However, implementations can include wired distribution, manual insertion of non-transitory computer readable storage medium, and unlocking a previously installed software object.

The word "exemplary" is used herein to mean serving as an example, instance, or illustration. Any aspect or design described herein as "exemplary" is not necessarily to be construed as preferred or advantageous over other aspects or designs.

Various aspects will be presented in terms of systems that may include a number of components, modules, and the like. It is to be understood and appreciated that the various systems may include additional components, modules, etc. and/or may not include all of the components, modules, etc. discussed in connection with the figures. A combination of these approaches may also be used. The various aspects disclosed herein can be performed on electrical devices including devices that utilize touch screen display technologies and/or mouse-and-keyboard type interfaces. Examples of such devices include computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Furthermore, the one or more versions may be implemented as a method, apparatus, or article of manufacture using standard programming and/or engineering techniques to produce software, firmware, hardware, or any combination thereof to control a computer to implement the disclosed aspects. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD), . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope of the disclosed aspects.

The steps of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure. Thus, the present disclosure is not intended to be limited to the aspects shown herein but is to be accorded the widest scope consistent with the principles and novel features disclosed herein.

In view of the exemplary systems described supra, methodologies that may be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described herein. Additionally, it should be further appreciated that the methodologies disclosed herein are capable of being stored on an article of manufacture to facilitate transporting and transferring such methodologies to computers. The term article of manufacture, as used herein, is intended to encompass a computer program accessible from any computer-readable device, carrier, or media.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

What is claimed is:

1. A method comprising:
   identifying as similar a second user of a second user device to a first user of a first user device, wherein the identified similarity between the first and second user is based upon a likeness between which previously acquired content items are permitted to be maintained in local memory on the first and second user devices by the first and second users, how the first and second users locally access the previously acquired content items on the first and second user devices, and/or how the first and second users locally organize the previously acquired content items within the local memory on the first and second user devices;

identifying content used by the second user device that has not been used by the first user device; and recommending the content to the first user device based on the identified similarity between the first and second users.

2. The method of claim 1, further comprising presenting a promotion for the content on a user interface of the first user device.

3. The method of claim 1, wherein recommending the content further comprises indicating to the first user that the second user was determined to be similar to the first user.

4. The method of claim 1, wherein identifying as similar the second user of the second user device to the first user of the first user device further comprises matching a demographic category of the first user and the second user.

5. The method of claim 1, wherein identifying as similar the second user of the second user device to the first user of the first user device based on the likeness between how the first and second users store the previously acquired content further comprises matching content on the first user device to content on the second user device.

6. The method of claim 5, wherein identifying as similar the second user of the second user device to the first user of the first user device based on the likeness between how the first and second users access the previously acquired content further comprises matching content used by the first user device to content used by the second user device.

7. The method of claim 6, wherein matching the content used by the first user device to content used by the second user device further comprises determining that a count of matching content exceeds a threshold.

8. The method of claim 6, wherein matching the content used by the first user device to content used by the second user device further comprises determining that a ratio of matching content exceeds a threshold.

9. The method of claim 1, wherein the content comprises a software application.

10. The method of claim 1, wherein the content comprises media content.

11. The method of claim 1, wherein the content comprises an advertisement for goods or services.

12. The method of claim 1, wherein identifying as similar the second user of the second user device to the first user of the first user device further comprises determining proximity of the first user and the second user.

13. The method of claim 12, wherein determining the proximity further comprises performing peer-to-peer networking between the first user device and the second user device.

14. The method of claim 13, further comprising provisioning the first user device with the content from the second user device via peer-to-peer networking.

15. The method of claim 12, wherein identifying as similar the second user of the second user device to the first user of the first user device further comprises receiving an allow indication from at least one of the first user device or the second user device.

16. The method of claim 1, wherein identifying as similar the second user of the second user device to the first user of the first user device and identifying the content used by the second user device that has not been used by the first user device further comprises processing data on a network remote to the first user device and the second user device.

17. The method of claim 16, wherein processing the data on the network that is remote to the first user device and the second user device further comprises communicating between the network and the first user device via a Wireless Wide Area Network (WWAN).

18. The method of claim 16, wherein processing the data on the network that is remote to the first user device and the second user device further comprises communicating between the network and the first user device via a Wireless Local Area Network (WLAN).

19. The method of claim 16, further comprising provisioning the first user device with the content from the network.

20. The method of claim 1, wherein the identifying identifies the identified similarity between the first and second users based on a similarity between frequencies in which the first and second users locally access a particular set of previously acquired content items via the first and second user devices, respectively.

21. The method of claim 1, wherein the identifying identifies the identified similarity between the first and second users based on the first and second users each storing a particular set of previously acquired content items in the local memory on the first and second user devices, respectively.

22. The method of claim 1, wherein the identifying identifies the identified similarity between the first and second users based on a similarity between browsing behaviors of the first and second users via the first and second user devices, respectively.

23. The method of claim 1, wherein the identifying identifies the identified similarity between the first and second users based on a similarity between content organizational habits of the first or second users for the previously acquired content in the local memory on the first and second user devices, respectively.

24. The method of claim 1, wherein the previously acquired content on the first and second user devices corresponds to content that has previously been downloaded to the first and second user devices, respectively.

25. At least one processor comprising:
a first module for identifying as similar a second user of a second user device to a first user of a first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

a second module for identifying content used by the second user device that has not been used by the first user device; and a third module for recommending the content to the first user device based on the identified similarity between the first and second users.

26. A non-transitory computer-readable storage medium comprising:
at least one instruction for causing a computer to identify as similar a second user of a second user device to a first user of a first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

at least one instruction for causing the computer to identify content used by the second user device that has not been used by the first user device; and at least one instruction for causing the computer to recommend the content to the first user device based on the identified similarity between the first and second users.

27. An apparatus comprising:

means for identifying as similar a second user of a second user device to a first user of a first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

means for identifying content used by the second user device that has not been used by the first user device; and means for recommending the content to the first user device based on the identified similarity between the first and second users.

28. An apparatus comprising:

an interface for selectively obtaining data about a population of users of user devices; and a content recommender for identifying as similar a second user of a second user device to a first user of a first user device based on the data, and identifying content used by the second user device that has not been used by the first user device based on the data, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices, and recommending the content to the first user device based on the identified similarity between the first and second users.

29. The apparatus of claim 28, further comprising a user interface of the first user device for presenting a promotion for the content.

30. The apparatus of claim 28, wherein the content recommender is further for recommending the content by indicating to the first user that the second user was determined to be similar to the first user.

31. The apparatus of claim 28, wherein the content recommender is further for identifying as similar the second user of the second user device to the first user of the first user device by matching a demographic category of the first user and the second user.

32. The apparatus of claim 28, wherein the content recommender is further for identifying as similar the second user of the second user device to the first user of the first user device based on the likeness between how the first and second users store the previously acquired content by matching content on the first user device to content on the second user device.

33. The apparatus of claim 32, wherein the content recommender is further for identifying as similar the second user of the second user device to the first user of the first user device based on the likeness between how the first and second users access the previously acquired content by matching content used by the first user device to content used by the second user device.

34. The apparatus of claim 33, wherein the content recommender is further for matching the content used by the first user device to the content used by the second user device by determining that a count of matching content exceeds a threshold.

35. The apparatus of claim 33, wherein the content recommender is further for matching the content used by the first user device to the content used by the second user device by determining that a ratio of matching content exceeds a threshold.

36. The apparatus of claim 28, wherein the content comprises a software application.

37. The apparatus of claim 28, wherein the content comprises media content.

38. The apparatus of claim 28, wherein the content comprises an advertisement for goods or services.

39. The apparatus of claim 28, wherein the interface is further for determining proximity of the first user and the second user.

40. The apparatus of claim 39, wherein the interface is further for determining the proximity by performing peer-to-peer networking between the first user device and the second user device.

41. The apparatus of claim 40, wherein the interface is further for provisioning the first user device with the content from the second user device via peer-to-peer networking.

42. The apparatus of claim 39, wherein the interface is further for receiving an allow indication from at least one of the first user device or the second user device.

43. The apparatus of claim 28, wherein the interface is further for communicating with a network that processes the data and is remote to the first user device and the second user device.

44. The apparatus of claim 43, wherein the interface is further for communicating with the network by communicating via a Wireless Wide Area Network (WWAN).

45. The apparatus of claim 43, wherein the interface is further for communicating with the network via a Wireless Local Area Network (WLAN).

46. The apparatus of claim 43, wherein the interface is further for provisioning the first user device with the content from the network.

47. A method comprising:

receiving, at a network, data associated with a first user of a first user device and a second user of a second user device of a population of user devices;

identifying as similar the second user of the second user device to the first user of the first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

identifying content used by the second user device that has not been used by the first user device; and recommending the content to the first user device based on the identified similarity between the first and second users.

48. At least one processor comprising:

a first module for receiving, at a network, data associated with a first user of a first user device and a second user of a second user device of a population of user devices;

a second module for identifying as similar the second user of the second user device to the first user of the first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

a third module for identifying content used by the second user device that has not been used by the first user device; and a fourth module for recommending the content to the first user device based on the identified similarity between the first and second users.

49. A non-transitory computer-readable storage medium comprising:

at least one instruction for causing a computer to receive, at a network, data associated with a first user of a first user device and a second user of a second user device of a population of user devices;

at least one instruction for causing the computer to identify as similar the second user of the second user device to the first user of the first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

at least one instruction for causing the computer to identify content used by the second user device that has not been used by the first user device; and at least one instruction for causing the computer to recommend the content to the first user device based on the identified similarity between the first and second users.

50. An apparatus comprising:

means for receiving, at a network, data associated with a first user of a first user device and a second user of a second user device of a population of user devices;

means for identifying as similar the second user of the second user device to the first user of the first user device, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices;

means for identifying content used by the second user device that has not been used by the first user device; and means for recommending the content to the first user device based on the identified similarity between the first and second users.

51. An apparatus comprising:

a network interface for receiving, at a network, data associated with a first user of a first user device and a second user of a second user device of a population of user devices;

a content recommender for identifying as similar the second user of the second user device to the first user of the first user device, and identifying content used by the second user device that has not been used by the first user device, recommending the content to the first user device based on the identified similarity between the first and second users, wherein the identified similarity between the first and second user is based upon a likeness between which previously acquired content items are permitted to be maintained in local memory on the first and second user devices by the first and second users, how the first and second users locally access the previously acquired content items on the first and second user devices and/or how the first and second users locally organize the previously acquired content items within the local memory on the first and second user devices.

\* \* \* \* \*